United States Patent [19]

Suzuki

[11] Patent Number: 5,172,677

[45] Date of Patent: Dec. 22, 1992

[54] DEVICE FOR DETERMINING ACTIVATION OF AN AIR-FUEL RATIO SENSOR

[75] Inventor: Hiroyoshi Suzuki, Himeji, Japan

[73] Assignee: Mitsubishi Denki Kabushiki Kaisha, Tokyo, Japan

[21] Appl. No.: 842,622

[22] Filed: Feb. 27, 1992

[30] Foreign Application Priority Data

Apr. 2, 1991 [JP] Japan .................................. 3-069846

[51] Int. Cl.$^5$ ............................................ F02D 41/14
[52] U.S. Cl. .................................... 123/688; 123/697
[58] Field of Search ................ 123/688, 697; 204/425, 204/426

[56] References Cited

U.S. PATENT DOCUMENTS

| | | | |
|---|---|---|---|
| 4,505,246 | 3/1985 | Nakajima et al. | 123/688 |
| 4,860,712 | 8/1989 | Nakajima et al. | 123/697 |
| 4,889,098 | 12/1989 | Suzuki et al. | 123/697 |
| 4,895,123 | 1/1990 | Uchinami et al. | 123/688 |
| 5,036,820 | 8/1991 | Fujimoto et al. | 123/688 X |
| 5,054,452 | 10/1991 | Denz | 123/688 X |

FOREIGN PATENT DOCUMENTS 0294355  12/1986  Japan .
0009357  1/1989   Japan .

Primary Examiner—Willis R. Wolfe
Attorney, Agent, or Firm—Sughrue, Mion, Zinn, Macpeak and Seas

[57] ABSTRACT

A device for determining activation of an air-fuel ratio sensor comprising an air-fuel ratio sensor arranged in an exhaust system of an engine and having a heater for heating an oxygen concentration cell element and an oxygen pump element, a current flowing means for flowing a predetermined current from a first electrode of the concentration cell to a reference electrode, a pump current controlling means for controlling current flowing in the pump element so that a sensor voltage between the reference electrode and the first electrode becomes a reference voltage, a pump current detecting means, a current flow cutting means, a sensor voltage detecting means, a heater power supplying means, and a timer means operated at every predetermined time interval for starting the heater supplying power means to the heater during a pump-current-cut state and for operating the current flow cutting means during the predetermined time interval. The air-fuel ratio controlling device determines the activation of the sensor by the difference between the sensor voltage before and after the current flow cutting means is operated and releases the pump-current-cut state when the sensor is determined to be activated.

1 Claim, 7 Drawing Sheets

DEVICE FOR DETERMINING ACTIVATION OF AN AIR-FUEL RATIO SENSOR

This invention relates to a device for determining activation of an air-fuel ratio sensor which detects an air-fuel ratio of an engine.

In recent times, a system is proposed wherein a whole area air-fuel ratio sensor is provided at an exhaust system to accurately control an air-fuel ratio of an intake mixture of an internal combustion engine to a target value over the whole area of the air-fuel ratio in use, which detects exhaust gas components correlating with the air-fuel ratio, and fuel supply quantity is controlled by a feed back control.

Since such an air-fuel ratio sensor does not function unless temperature of a sensor element unit thereof is elevated to about 400° to 500° C. or more, a heater is provided which heats up the sensor element unit and maintains the temperature of the sensor element unit above an activation temperature.

However, when the engine is started up from a state wherein the sensor temperature is low, the sensor may be destructed unless it is utilized after confirming that the sensor unit temperature is above the activation temperature after the heater is initiated.

Various determining methods are proposed for determining the activation of the air-fuel sensor. Among these, for instance, a method is known which determines that the activation of the sensor is completed when a predetermined time elapses after heating of the sensor is performed, as disclosed in Japanese Unexamined Patent Publication No. 241652/1986, or a method is known which determines that the sensor is activated when an inter-electrode voltage between a cell element and a pump element falls in a predetermined range when current is flown in the pump element of the sensor.

Next, explanation will be given to this conventional device for determining activation of an air-fuel ratio sensor. FIG. 5 is a construction diagram of a conventional engine control system which performs an air-fuel ratio control utilizing the air-fuel sensor. FIG. 6 is a construction diagram of a conventional engine control system which performs the air-fuel control, and FIG. 7 designates timing charts for explaining a method of initiating the conventional sensor when the sensor is to be initiated.

Explanation will be given utilizing FIGS. 5 to 7. First, in FIG. 5, a reference numeral 1 designates an air-fuel sensor, which is installed at an exhaust pipe 31 of an engine 30, 2, a sensor control amplifier of the air-fuel sensor 1, 3, an engine revolution sensor, 4, an intake quantity sensor, 5, a cooling water temperature sensor of the engine 30, 6, a fuel injection valve, 7, an air-fuel ratio control device, 8, a throttle valve, 9, a throttle opening degree sensor of the throttle valve 8, and 32, an intake pipe.

In FIG. 5, the engine revolution sensor 3 detects an engine revolution number Ne, the intake quantity sensor 4, an intake quantity Qe, the throttle opening degree sensor 8, a throttle opening degree $\theta$, and the cooling water temperature sensor 5, a cooling water temperature WT. These detected values are respectively outputted to the air-fuel ratio control device 7, and are state quantities showing running condition of the engine 30.

The air-fuel ratio of a mixture of intake air introduced to the control valve 8, and fuel injected from the fuel injection valve 6 at the intake pipe 32, is detected by the air-fuel ratio sensor 1 installed at the exhaust pipe 31, utilizing the sensor control amplifier 2. An output of the air-fuel ratio is transmitted similarly to the air-fuel ratio control device 7 from the sensor control amplifier 2.

Next, explanation will be given to FIG. 6. The air-fuel ratio sensor 1 is composed of a sensor element unit 11 and a heater 12. The sensor element unit 11 is composed of an oxygen pump element 11a, an oxygen concentration cell element 11b, a diffusion chamber 11c, and an atmospheric chamber 11d. The sensor control amplifier 2 is composed of a differential integral amplifier 21 as a pump current controlling means, a differential amplifier 22 as a pump current detecting means, a non-inverting amplifier 23, a non-inverting amplifier 29 as a pump voltage detecting means, the cut transistor 25 as the pump current cutting means, and a heater control circuit 28.

In this sensor control amplifier 2, an output of the differential integral amplifier 21 is connected to the oxygen pump element 11a through a current detecting resistance RS, and a both terminal voltage of the current detecting resistance RS is inputted to the differential amplifier 22.

In the non-inverting amplifier 23, an output terminal of the differential amplifier 22 is connected to a non-inverting input terminal thereof, and an offset voltage $V_{OB}$ is applied to the non-inverting input terminal. In the non-inverting amplifier 29, an applied voltage of the oxygen pump element 11a is applied to a non-inverting input terminal, and an offset voltage $V_{PB}$, to an inverting input terminal, respectively.

Next, explanation will be given to the air-fuel ratio control device 7. This air-fuel ratio control device 7 is composed of multiplexors 71a and 71b, analogue/digital (hereinafter A/D) converters 72a and 72b, and input interface (hereinafter I/F) 73, a microprocessor (hereinafter $\mu$-P) 74, a read only memory (hereinafter ROM) 75, a random access memory (hereinafter RAM) 76, output I/Fs 77a and 77b, and a fuel injection valve drive circuit 78.

In this air-fuel ratio control device, the engine revolution number Ne which is an output of the engine revolution sensor 3 is transmitted to the $\mu$-P 74 through the input I/F 73, the intake quantity Qa which is detected by the intake quantity sensor 4, and the cooling water temperature WT which is detected by the cooling water temperature sensor 5, respectively through the multiplexor 71b and the A/D converter 72b.

Outputs of the non-inverting amplifier 23 and the non-inverting amplifier 29 of the sensor control amplifier 2, that is, the air-fuel ratio output $V_O$ and the pump voltage output $V_{PO}$ are transmitted to the $\mu$-P 74 through the multiplexor 71a and the A/D converter 72a.

Furthermore, the fuel injection valve 6 is connected to the fuel injection valve drive circuit 78, and is controlled by the fuel injection valve drive circuit 78 through the output I/F 77b as well as the cut transistor 25 and the heater control circuit 26 of the sensor control amplifier 2.

Next, explanation will be given to the operation of the conventional device for determining activation of the air-fuel ratio sensor. In a state wherein the engine 31 is driven, the heater 12 of the air-fuel sensor 1 is controlled to operate by the heater control circuit 28, and the sensor element unit 11 is activated, the oxygen concentration cell element 11b generates an electromotive force $V_S$ which corresponds with a difference between oxygen concentration in the diffusion chamber 11c and that in the atmospheric chamber 11e.

When this sensor electromotive force $V_S$ is controlled by flowing a pump current Ip to the oxygen pump element 11a so that it becomes the reference voltage Vref through the differential integral amplifier 21, the pump current $I_P$ is proportional to the air-fuel ratio. At this occasion, this pump current $I_P$ is detected by the detecting resistance RS, which is amplified by the differential amplifier 22, and provided with an offset voltage $V_{OB}$, by which the air-fuel ratio output $V_O$ is obtained.

The direction of the offset voltage $V_{OB}$ differs between in case of an excessively rich zone of the air-fuel ratio and that of an excessively lean zone thereof. Therefore, the offset voltage of $V_{OB}$ is provided to make the air-fuel ratio output $V_O$ a positive output irrespective of the direction of the pump current Ip.

The air-fuel ratio control device 7 calculates a target air-fuel ratio by the μ-P 74 from informations of the revolution number Ne, intake quantity Qa, the throttle opening degrees θ and the cooling water temperature WT based on programs and data previously memorized in the ROM 75.

The air-fuel ratio control device 7 performs a feed back control so that the air-fuel ratio of the engine 30 becomes the target air-fuel ratio by correcting a valve opening time of the fuel injection valve 6, based on a deviation of the target air-fuel ratio from an actual air-fuel ratio which is converted from the measured air-fuel ratio output $V_O$ and by injecting fuel from the fuel injection valve 6 corresponding to the valve opening time. The RAM 76 is utilized for memorizing the data temporarily at this occasion.

FIG. 7 illustrates timing charts when the air-fuel ratio sensor is initiated. Explanation will be given to an example wherein the air-fuel ratio is rich after the engine is started. The heater 12 of the air-fuel ratio sensor 1 starts heating by a drive order which is given to the heater control circuit 26 by the μ-P 74 through the output I/F 77a simultaneously with the starting of the engine 30.

At this occasion, in a range of the temperature $T_S$ of the sensor element unit 11 of about 400° C., since the electromotive force $V_S$ of the oxygen concentration cell element 11b stays low, input deviation of the differential integral amplifier 21 is large. Accordingly, a large pump voltage $V_P$ is applied to the pump element 11a.

The pump voltage output $V_{PO}$ becomes a positive output since the pump voltage $V_P$ is added with offset voltage $V_{PB}$ by the non-inverting amplifier 29. Since impedance of the pump element 11a is high, almost no pump current $I_P$ is flown, and the air-fuel ratio output $V_O$ is almost equal to the offset voltage $V_{OB}$.

Further, when the temperature $T_S$ approaches to about 400° to 500° C., since the electromotive force $V_S$ of the oxygen concentration cell element 11b is increased to the reference voltage Vref, the sensor electromotive force $V_S$ is controlled constant to the reference Vref. Therefore, the pump voltage $V_P$ converges in the direction wherein oxygen is supplied to the defusing chamber 11c, that is, in the direction wherein $V_{PO} \leq V_{PB}$, and the pump current $I_P$, gradually to a current value showing current air-fuel ratio, and the convergence is completed at the temperature TS of about 700° C.

Accordingly, conventionally, as is illustrated in FIG. 7, to detect the activation point, an activation determining method is proposed wherein the activation is determined when the pump voltage output $V_{PB}$ falls in a predetermined allowable voltage of $V_{PB} \pm \Delta V_{PB}$, or an activation determining method is proposed wherein the sensor is determined to be activated, when the difference $\Delta V_S$ between the sensor electromotive force $V_S$ and the reference voltage Vref falls in a predetermined range and a pump voltage output $V_{PO}$ falls in a predetermined allowable voltage range of $V_{PB} \pm \Delta V_{PB}$.

Since the conventional device for determining activation of an air-fuel ratio sensor is composed as above, a large voltage is continuously applied to the oxygen pump element 11a in a state wherein temperature of the sensor element unit 11 is low. Therefore deterioration of the sensor is accelerated, and durability of the sensor is low.

To solve the above problem, a method is proposed wherein a timer is provided after the initiation of the air-fuel sensor, the pump current stops flowing to the oxygen pump element 11a, and the pump current restarts flowing to the oxygen pump element 11a by making the cut transistor 25 OFF after the timer period is terminated.

However, an index of the sensor characteristics can not be obtained during the timer period. Accordingly, in case that a running condition of the engine changes after the staring up of the engine, and the temperature elevation of the sensor element unit 11 is reduced, the sensor may not be activated even after the timer periods is terminated. On the contrary, when the temperature elevation of the element unit 11 is fast such as in case that the engine is restarted after running thereof, the timer period may not be terminated regardless of the air-fuel sensor 1 being already activated. Therefore, the accurate determination of the activation point is difficult.

It is an object of the present invention to solve above problems. It is an object of the present invention to provide a device for determining activation of an air-fuel ratio sensor capable of detecting accurately the activation point of the air-fuel sensor without deteriorating the air-fuel sensor.

According to an aspect of the present invention, there is provided a device for determining activation of an air-fuel ratio sensor which comprises: an air-fuel ratio sensor comprising a diffusion chamber arranged at an exhaust system of an engine wherein exhaust gas of the engine is diffused and introduced and a heater which heats an oxygen concentration cell element and an oxygen pump element respectively made of an oxygen-ion-conductive-solid-electrolyte material and respectively provided with first ones of pairs of electrodes interposing the diffusion chamber; a current flowing means for flowing a predetermined current from a second one of the pair of electrodes of the oxygen concentration cell to the first one of the pair of electrodes thereof on the side of the diffusion chamber so that the second one of the pair of electrodes of the oxygen concentration cell becomes a reference electrode; a pump current controlling means for controlling a pump current flowing in the oxygen pump element so that a sensor voltage between the reference electrode of the oxygen concentration cell and the first one of the pair of electrodes thereof on the side of the diffusion chamber becomes a predetermined reference voltage; a pump current detecting means for detecting the pump current; a current flowing cutting means for cutting the current flowing means; a sensor voltage detecting means for detecting the sensor voltage; a heater power supplying means for supplying power to the heater; a timer means for starting supplying power to the heater from the heater power supplying means in a pump-current-cut state and for operating the current flowing cutting means during a predetermined time interval from when the heater starting supplying power means is operated at every predetermined time interval; and an air-fuel ratio controlling device which determines activation of the air-fuel ratio sensor by a difference of the sensor voltage between before and after the current flowing means is operated and controls to release the pump-current-cut state when the air-fuel ratio sensor is determined to be activated.

In this invention, first, the current flowing means for flowing current to the oxygen concentration cell element is made operative. Power being to flow in the heater from the heater power supplying means in a pump-current-cut state. The current flowing cutting means is operated from the starting of operation at every predetermined period by the timer means. The activation of the air-fuel ratio sensor is determined by the difference between the sensor voltages before and after the cutting the current flowing means and thereafter controls to release the pump-current-cut state when the air-fuel ratio sensor is determined to be activated.

Figure 1:
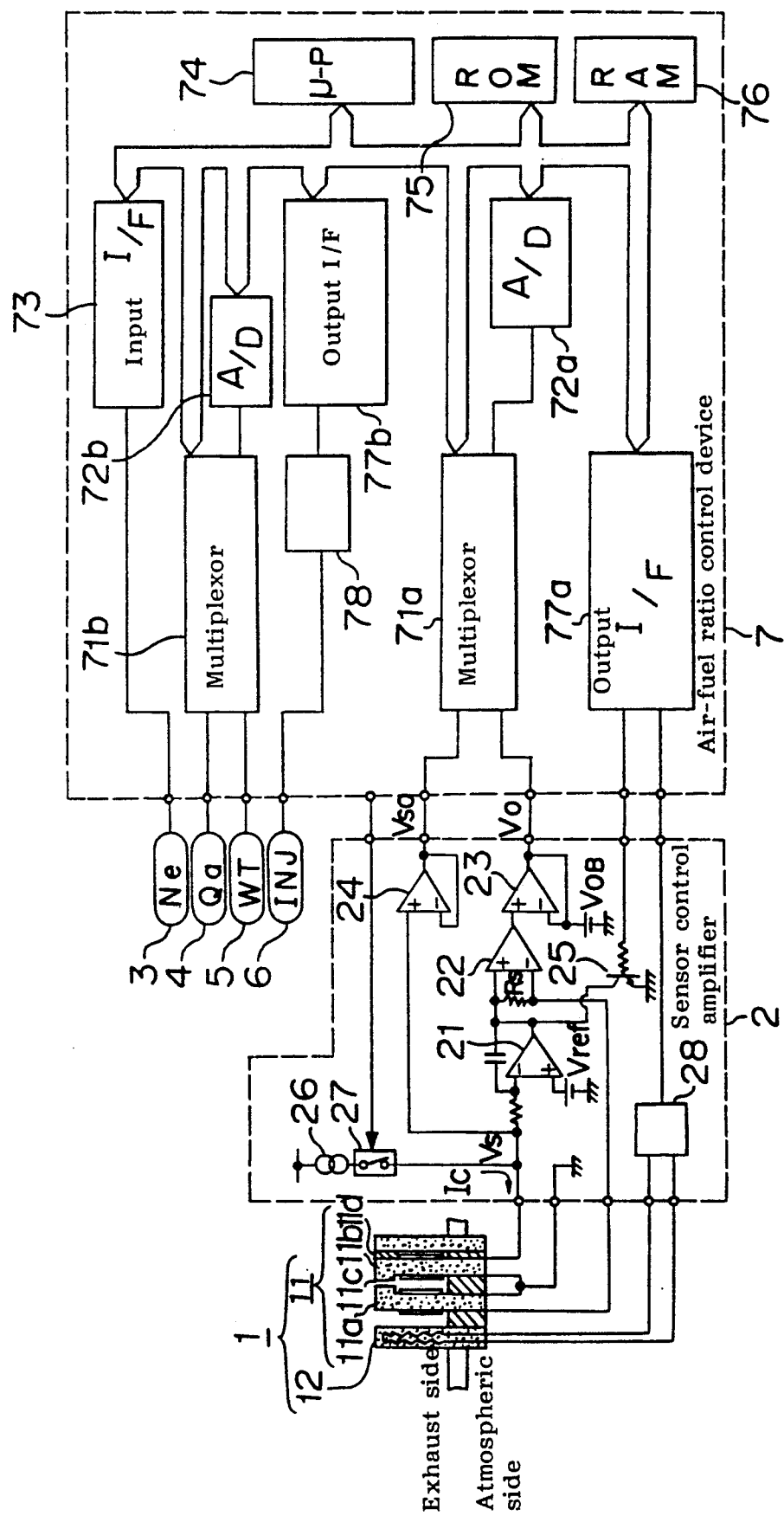
FIG. 1 is a block diagram showing construction of an embodiment of a device for determining activation of an air-fuel ratio sensor according to the present invention.

Explanation will be given to embodiments of the device for determining activation of an air-fuel ratio sensor of the present invention based on the drawings as follows. FIG. 1 is block diagram showing construction of an embodiment of the invention. The same notation is attached to the same part in FIG. 6, and explanation to the construction is omitted. Explanation will be made mainly on parts which are different from those in FIG. 6.

Figure 6:
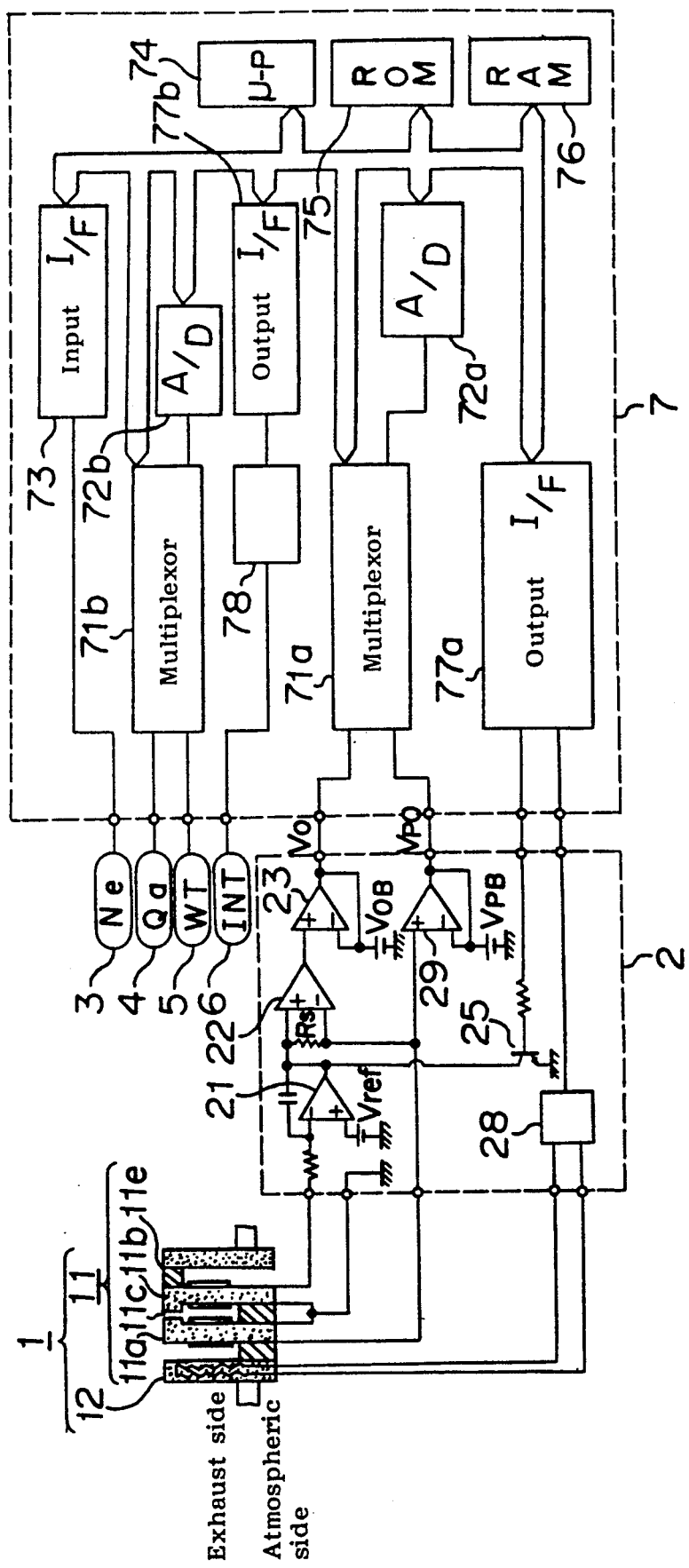
FIG. 6 is a block diagram showing construction of the conventional device for determining activation of air fuel ratio sensor.
Figure 7:
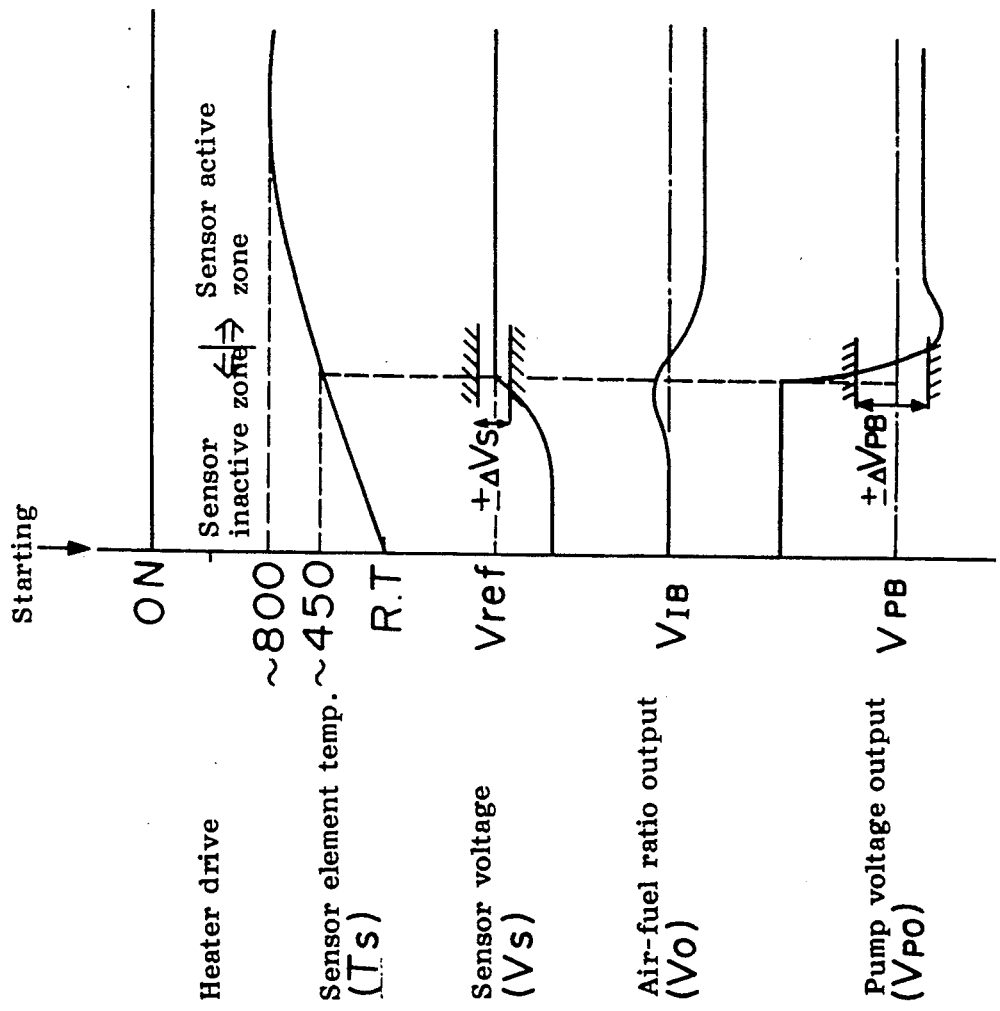
FIG. 7 illustrates timing charts showing an activation determination of an air-fuel ratio sensor of the conventional device for determining activation of the air-fuel ratio sensor.

As apparent by comparing this FIG. 1 with FIG. 6, in FIG. 1, parts of new notations 24, 26, 27 and 11d are added to the construction of FIG. 6, and the other construction is the same as in FIG. 6.

A reference numeral 11d designates a reference electrode space which an electrode faces which pairs with another electrode which faces the diffusion chamber 11c of the oxygen concentration cell element 11b.

Furthermore, a reference numeral 24 designates a sensor voltage detecting means, and in this embodiment, a non-inverting amplifier is utilized. A (−) input terminal of the non-inverting amplifier 24 is connected to an output terminal thereof, and a sensor voltages $V_S$ is connected to a (+) input terminal.

A reference numeral 26 designates a current flowing means which is connected to the reference electrode of the oxygen concentration cell element 11b, and in this embodiment, is a constant current source. Current supply from this constant current source 26 to the oxygen concentration cell element 11b is cut by a cell current cutting means 27.

Figure 2:
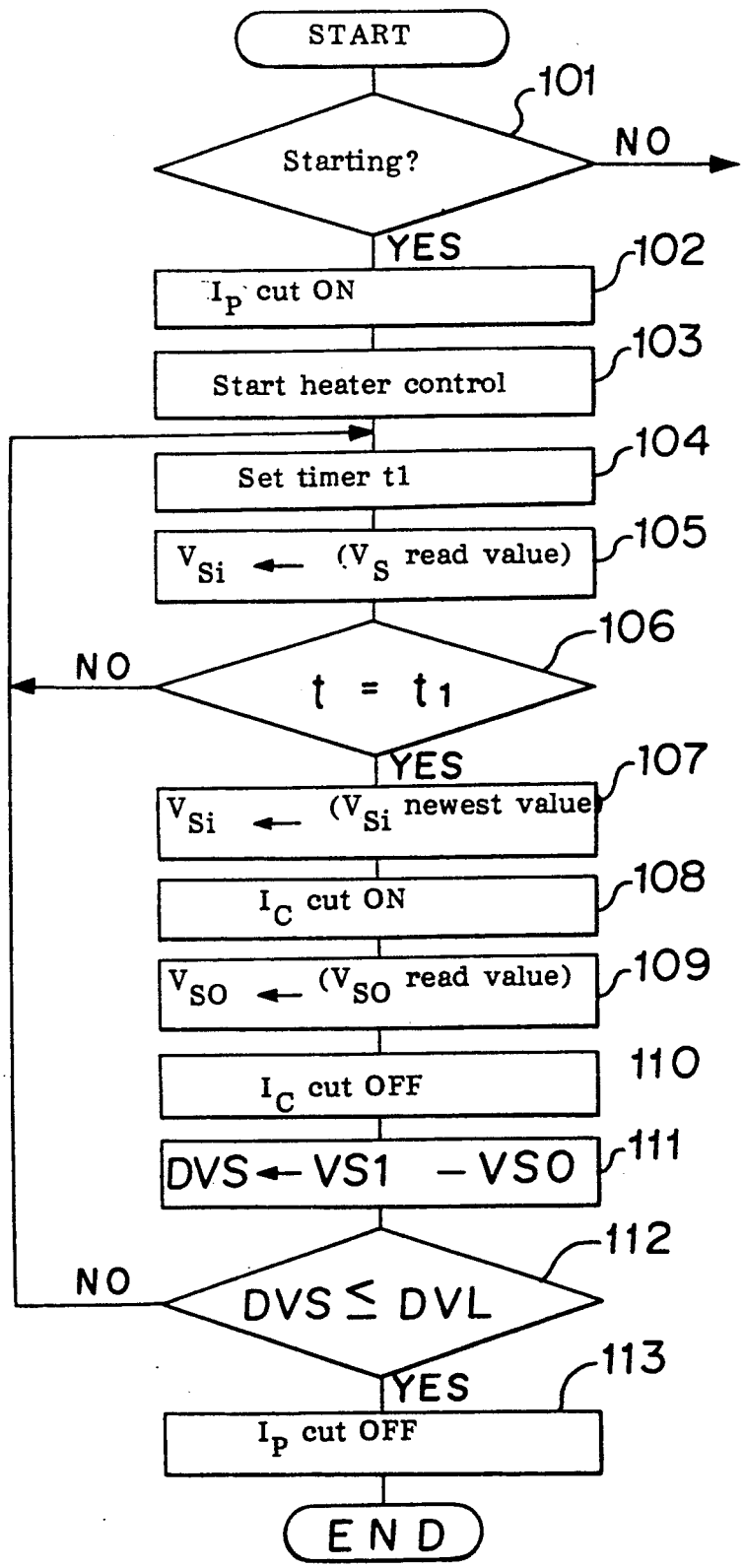
FIG. 2 is a flow chart showing a procedure for performing an activation determination by the device for determining activation of an air-fuel ratio sensor of FIG. 1.
Figure 3:
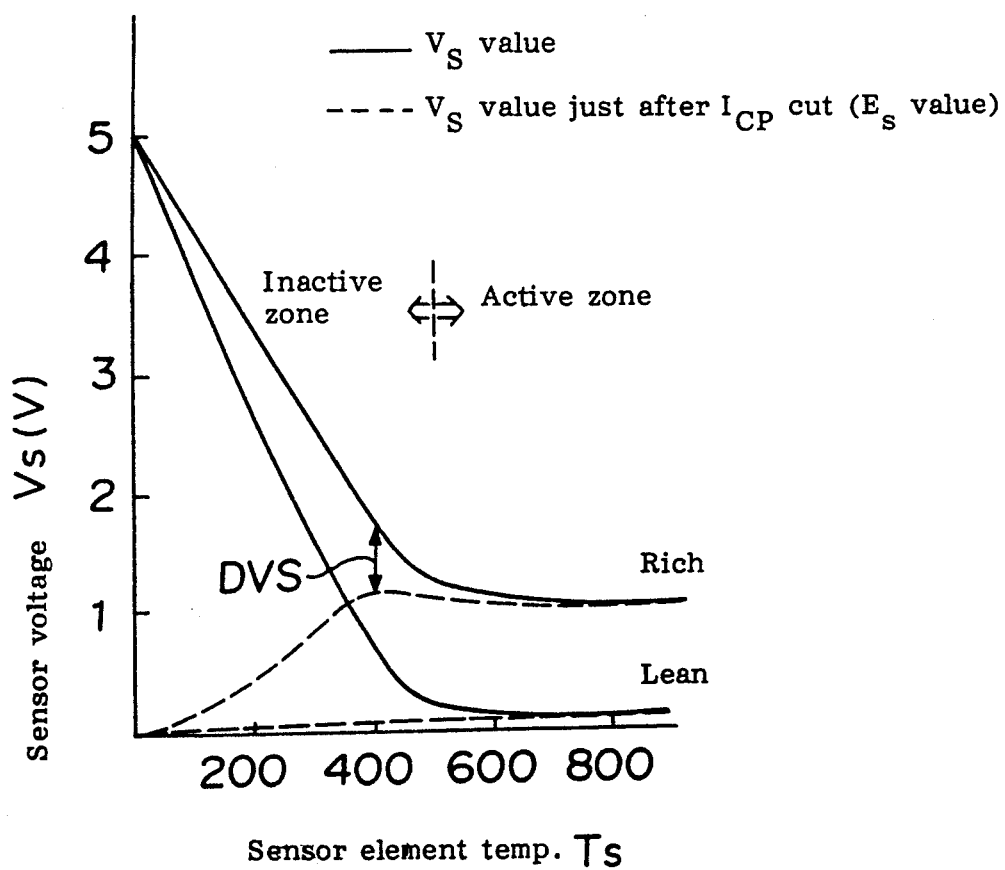
FIG. 3 is an explanatory diagram showing a relationship between a sensor temperature and a sensor voltage of the air-fuel ratio sensor of the device for determining activation of the air-fuel ratio sensor of FIG. 1.
Figure 4:
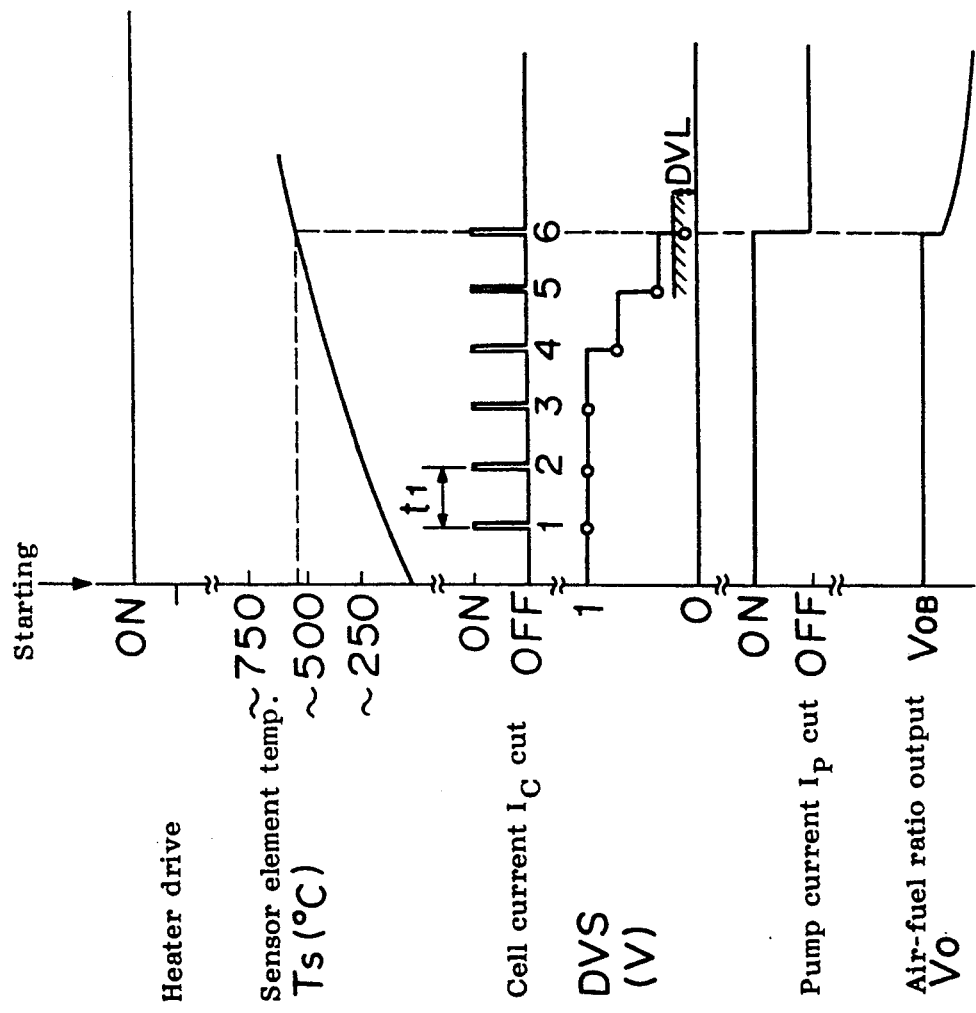
FIG. 4 illustrates timing charts showing the activation determination of the air-fuel ratio sensor by the device for determining activation of the air-fuel ratio sensor of FIG. 1.

FIG. 2 is a flow chart showing a procedure for determining activation of the air-fuel ratio sensor of this invention, FIG. 3, an explanatory diagram showing a relationship between the sensor temperature $T_S$ and the sensor voltage $V_S$, and FIG. 4, timing charts for showing the activation determination of the air-fuel ratio sensor.

Figure 5:
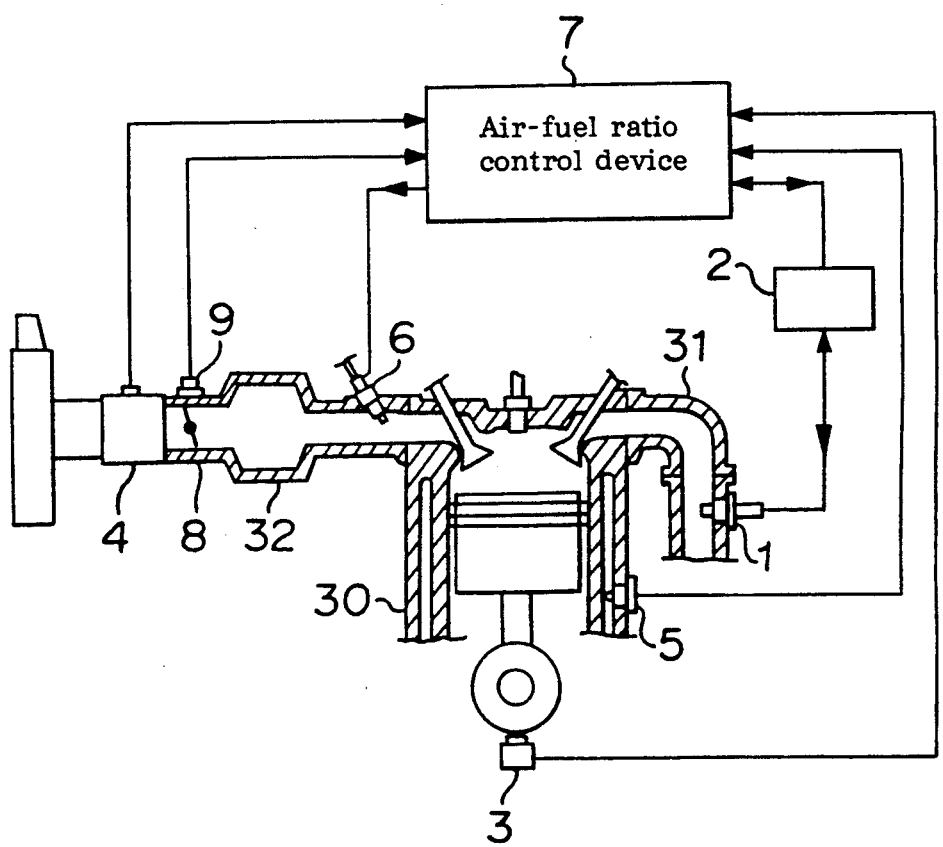
FIG. 5 is a construction diagram of a conventional engine control system.

Next, explanation will be given to the operation of the present invention utilizing FIGS. 2 to 4. In a state wherein the engine 30 shown in FIG. 5 is operated, the heater 12 of the air-fuel ratio sensor 1 shown in FIG. 1 is controlled to operate by the heater control circuit 28, and the sensor element unit 11 is activated, oxygen is brought to the reference electrode space 11d of the oxygen concentration cell element 11b, by a current $I_C$ which is flown from the constant current source 26 to an electrode on the side of the defusing chamber 11c through an electrode on the side of the reference electrode space 11d.

The reference electrode space 11d is very small in volume and is made so that leakage is minimized. Therefore partial pressure of oxygen on the side of the reference electrode 11d is maintained in an order of several percent by the cell current $I_C$ of the order of several tens $\mu A$. The oxygen concentration cell element 11d operates similarly as the conventional oxygen concentration cell element of which reference electrode space is the atmosphere, and a voltage of about 100 mV is generated between the electrodes when the exhaust gas defusing chamber 11C is lean, and if it is rich, about 1 V.

When this sensor voltage $V_S$ is controlled so that it becomes a predetermined reference voltage $V_{ref}$ through the differential integral amplifier 21 of the control amplifier 2, by flowing a pump current $I_P$ to the oxygen pump element unit 11a, the pump current $I_P$ is proportional to the air-fuel ratio.

At this occasion, the pump current $I_P$ is detected by the detecting resistance $R_S$, which is amplified by the differential amplifier 22, provided with the offset voltage $V_{OB}$, by which the air-fuel ratio output $V_O$ is obtained.

Furthermore, the sensor voltage $V_S$ is amplified by the non-inverting amplifier 24, A/D-converted by the A/D converter 72a through the multiplexor 71a, and is read in the $\mu$-P 74 as well as the sensor voltage output $V_{SO}$. In this case the non-inverting amplifier 24 is a buffer amplifier of Gain "1", and $V_{SO}=V_S$.

In the air-fuel ratio control device 7, a feed back control is performed utilizing the air fuel ratio output $V_O$ as in the conventional case, so that air-fuel ratio of the engine 30 becomes a target air-fuel ratio, when the air-fuel ratio sensor 1 is activated.

When the engine 30 is started, first, the operation determines whether the engine is in starting mode, by the $\mu$-P 74 of the air fuel ratio control device 7, in step 101 of FIG. 2. When the engine is in starting mode, the operation makes the cut transistor 25 of the sensor control amplifier 2 ON, through the output I/F 77a in step 102, and performs the pump-current-cut (I$_P$ cut) wherein the cut transistor 25 of the sensor control amplifier 2 is made ON, and the oxygen pump element 11a is earthed, so that the pump current is not flown in the oxygen pump element, and goes to step 103.

In step 103, the operation initiates the heater control circuit 28 similarly through the output I/F 77a, by which power is supplied to the heater 12, and heating of the sensor element unit 11 is started.

Next, in step 104, the operation sets a predetermined time t1 by a timer as shown in FIG. 4. In step 105, the operation reads the sensor voltage V$_S$, which is memorized in the RAM 76 as data V$_{Si}$. In step 106, the operation renews the data V$_{Si}$ until the time t1 elapses.

The sensor voltage V$_S$ is defined by the following equation assuming an internal resistance of the oxygen concentration cell element 11b as RS, an electromotive force as ES, and utilizing the cell current I$_C$.

$$V_S = RS \times I_C + ES \tag{1}$$

When the time t1 elapses, the newest data V$_{Si}$ of the sensor voltage just before the elapse of the time t1 is memorized in the RAM 76 as V$_{S1}$, in step 107. In step 108, the operation operates a current flowing cutting means 27 through the output I/F 77b, by which the cell current to the oxygen concentration cell element 11b is cut. In step 109, the operation reads the sensor voltage V$_S$ at this time, which is memorized as V$_{SO}$. In step 110, the operation switches the current flowing cutting means 27, by which flowing cell current I$_C$ to the oxygen concentration cell element 11b is restarted.

The sensor voltage V$_S$ which is memorized as the sensor voltage output V$_{SO}$ when the cell current I$_C$ is cut, agrees with a value wherein I$_C$=0 in the above equation (1) that is, it agrees with the electromotive force ES.

Since oxygen supply to the reference electrode space 11d is cut and the partial pressure of oxygen in the reference electrode space 11d gradually decreases, the electromotive force ES of the oxygen concentration cell element 11d decreases with time correspondingly. However, as mentioned above, the leakage from the reference electrode space 11d is very little. Therefore a time lag in the decreasing of the electromotive force ES is in the order of several seconds. On the contrary, it takes several tens msec at most from the cutting of the cell current to the reflowing thereof. Therefore, the sensor voltage V$_S$ does not change between just before the cutting of the cell current I$_C$ and just after the reflowing. The change of the sensor voltage V$_S$ is not influenced by the cutting of the cell current I$_C$.

Next, in step 111, The operation calculates a difference DVS between the sensor voltage V$_{S1}$ and V$_{SO}$. The difference DVS becomes RS×I$_C$. The cell current I$_C$ is constant. Therefore it signifies the change in the internal resistance. Therefore, the operation determines that the sensor is activated when the difference is a previously memorized predetermined value DVL or less, that is, when the internal resistance RS is a predetermined value in step 112 or less, and goes to step 113.

In step 113, the operation makes the cut transistor 25 off, releases the pump current cutting, performs the sensor voltage constant control, and detects the air-fuel ratio output V$_O$ of the activated air-fuel ratio sensor 1. When the difference DVS is above the predetermined value DVL the operation interates the treatment in steps 104 to 112.

In FIG. 3, the sensor voltage V$_S$ and the sensor voltage just after the cutting of the cell current, that is, the electromotive force ES, when the sensor element temperature T$_S$ is changed in cases of rich air-fuel ratio and lean air-fuel ratio, are measured, and respectively shown by the bold line and the broken line. The difference between the bold line and the broken line is the difference DVS, that is, a value corresponding with the internal resistance R$_S$.

As shown in this FIG. 3, the electromotive force E$_S$ can be known by the air-fuel ratio and the element temperature T$_S$, but internal resistance RS depends only on the element temperature T$_S$, which is rapidly reduced at about 400° to 500° C. Accordingly, the determination of the activation temperature of the sensor element can accurately be performed by setting the comparison value DVL corresponding with the internal resistance value for the activation temperature.

In this Example, as stated below, the difference DVS at the element temperature of about 500° C., of about 200 mV (the internal resistance value at this occasion is several kΩ which is determined by conversion of the cell current) is set as the comparison value DVL.

FIG. 4 illustrates timing charts showing the activation determination when the engine is started, in the above Example. The change of the sensor element temperature T$_S$ after the heater 12 is operated in a state wherein the pump current is cut with the starting of the engine 30, and the change of the difference DVS which is obtained by the difference between the sensor voltages V$_S$'s before and after the cutting of the cell current I$_C$ for a very short time at the interval of the time t1 which is set by the timer, making the displayed maximum value as 1 V, are shown.

In FIG. 4, the difference DVS is below the comparison value DVL (about 200 mV) wherein the element temperature is about 500° C., at the sixth flowing current cutting time, by which the activation determination is performed, and the pump current cutting is released, whereby the air-fuel ratio output V$_O$ converges to an output value showing an air-fuel ratio at that time point, from the offset voltage value V$_{OB}$ at the pump current cut time.

According to the above example, in an activation state wherein the sensor element temperature is low in which the sensor electromotive force constant control is not established, since voltage is not applied to the oxygen pump element 11a by the pump current cutting, it has an advantage wherein the air-fuel ratio sensor is not deteriorated and destructed by the activation determination treatment.

Furthermore, since the determination is performed by the internal resistance RS of the concentration cell element 11b which is a function of the sensor element temperature T$_S$ and which does not depend on the current air-fuel ratio, it has an advantage wherein the activation determination can accurately be performed irrespective of the starting air-fuel ratio.

In the above example, the period of the time t1 is made constant. However, when it is a decreasing function of the cooling water temperature WT, utilizing the cooling water temperature WT detected by the cooling water temperature sensor 5, it has an advantage wherein the activation determination is not retarded by the timer, since the time period t1 is reduced, in case that a cooling water temperature WT is elevated, even when the temperature of the exhaust pipe 31 to which the air-fuel ratio sensor 1 is attached, is comparatively high and increase of the exhaust gas temperature is fast, as in the restarting of the engine in a short time after running thereof.

Furthermore, in the above example, as the sensor voltage $V_S$ which is utilized in the activation determination, a value just before the elapse of the time t1 is utilized among the sensor voltage $V_{Si}$'s which are measured in the period of the time t1. However, since the period of the time t1 is previously determined, the sensor voltage $V_S$ which is measured only at one time just before the elapse of the time t1, may be utilized.

As mentioned above, according to the present invention, the current flowing means which flows current to the oxygen concentration cell element of the air-fuel ratio sensor which comprises the diffusion chamber, the oxygen concentration cell element, the oxygen pump element and the heater, is made operative, in a pump-current-cut state, the power supply to the heater from the heater power supplying means is initiated, and the activation state of the air-fuel ratio sensor is determined by the difference of the sensor voltage between before and after the current flowing cutting by operating the current flowing cutting means at every predetermined interval by the timer means from when the power supply to the heater is started. The pump-current-cut state is released only when the activation is determined. Therefore, the air-fuel ratio sensor is not deteriorated and destructed by the treatment of the activation determination, and the activation determination can accurately be performed irrespective of the starting air-fuel ratio.

I claim:

1. A device for determining activation of an air-fuel ratio sensor which comprises:

an air-fuel ratio sensor comprising a diffusion chamber arranged at an exhaust system of an engine wherein exhaust gas of the engine is diffused and introduced and a heater which heats an oxygen concentration cell element and an oxygen pump element respectively made of an oxygen-ion-conductive-solid-electrolyte material and respectively provided with first ones of pairs of electrodes interposing the diffusion chamber;

a current flowing means for flowing a predetermined current from a second one of the pair of electrodes of the oxygen concentration cell to the first one of the pair of electrodes thereof on the side of the diffusion chamber so that the second one of the pair of electrodes of the oxygen concentration cell becomes a reference electrode;

a pump current controlling means for controlling a pump current flowing in the oxygen pump element so that a sensor voltage between the reference electrode of the oxygen concentration cell and the first one of the pair of electrodes thereof on the side of the diffusion chamber becomes a predetermined reference voltage;

a pump current detecting means for detecting the pump current;

a current flowing cutting means for cutting the current flowing means;

a sensor voltage detecting means for detecting the sensor voltage;

a heater power supplying means for supplying power to the heater;

a timer means for starting supplying power to the heater from the heater power supplying means in a pump-current-cut state and for operating the current flowing cutting means during a predetermined time interval from when the heater starting supplying power means is operated at every predetermined time interval; and an air-fuel ratio controlling device which determines activation of the air-fuel ratio sensor by a difference of the sensor voltage between before and after the current flowing means is operated and controls to release the pump-current-cut state when the air-fuel ratio sensor is determined to be activated.

* * * * *